United States Patent [19]
Griffiths et al.

[11] Patent Number: 5,701,009
[45] Date of Patent: Dec. 23, 1997

[54] GAS DETECTION DEVICES

[75] Inventors: Richard F. Griffiths, Altrincham; Christopher David Jones, Salisbury, both of United Kingdom

[73] Assignee: The Secretary of State for Defence in Her Britannic Majesty's Government of the United Kingdom of Great Britain and Northern Ireland of Defence and Evaluation Research Agency, Hants, United Kingdom

[21] Appl. No.: 513,886
[22] PCT Filed: Mar. 3, 1994
[86] PCT No.: PCT/GB94/00411
  § 371 Date: Sep. 18, 1995
  § 102(e) Date: Sep. 18, 1995
[87] PCT Pub. No.: WO94/20845
  PCT Pub. Date: Sep. 15, 1994

[30] Foreign Application Priority Data

| Mar. 5, 1993 | [GB] | United Kingdom | 9304553 |
| Apr. 26, 1993 | [GB] | United Kingdom | 9308615 |
| May 25, 1993 | [GB] | United Kingdom | 9310785 |

[51] Int. Cl.$^6$ ................................................. G01F 1/64
[52] U.S. Cl. ............................. 250/356.1; 73/861.09
[58] Field of Search ........................... 250/287, 356.1; 73/861.09; 324/464

[56] References Cited

U.S. PATENT DOCUMENTS

| 3,688,106 | 8/1972 | Brain | 250/356.1 |
| 3,718,043 | 2/1973 | Fishman et al. | 250/356.1 |
| 4,304,124 | 12/1981 | Biblarz | 73/861.09 |
| 4,393,719 | 7/1983 | Wiegand et al. | 73/861.09 |
| 5,047,723 | 9/1991 | Puumalainen | 324/464 |
| 5,455,417 | 10/1995 | Sacristan | 250/287 |

FOREIGN PATENT DOCUMENTS

| 0 160 888 A3 | 11/1985 | European Pat. Off. . |
| 0 524 022 A1 | 1/1993 | European Pat. Off. . |
| 1 238 910 | 7/1971 | United Kingdom . |
| 87/07720 | 12/1987 | WIPO . |
| 92/07255 | 4/1992 | WIPO . |

*Primary Examiner*—Jack I. Berman
*Attorney, Agent, or Firm*—Nixon & Vanderhye P.C.

[57] ABSTRACT

Gas detector includes structure (10) defining a gas flow passage (11), means (12) for passing an ultraviolet light beam (13) across the passage, and first and second electrodes (16, 17) downstream of the ultraviolet light means (12), at least one of the first and second electrodes (16, 17) being in the form of a series of electrically separate segments (16a, 17a) extending in a downstream direction, the electrodes (16, 17) being connectable to potential applying means (18) and to means (20) whereby the current passing through each segment (16a, 17a) of a segmented electrode (16, 17) can be measured.

8 Claims, 2 Drawing Sheets

GAS DETECTION DEVICES

BACKGROUND OF THE INVENTION

1. Field of the Invention

The present invention relates to gas detection devices, particularly those of the type which use the ionisation of gases by ultra-violet light. One use of such devices is in the detection and investigation of gas flows, when a tracer gas is introduced into a main gas flow. Another is in the detection of the presence of an extraneous gas in a flow of a particular gas.

2. Discussion of Prior Art

The main gas flow with which these devices is used is of air, and this specification will therefore, for convenience, refer to the main gas flow as airflow. Similarly, for convenience, any other gas in the airflow, whether a tracer gas or an extraneous gas, will be referred to as a test gas.

Devices of this type operate by passing the airflow through an ultra-violet light from a lamp which is preferably tuned for maximum ionisation effect on the test gas, and measuring the current flow between two electrodes caused by ionisation of the gas as the airflow is passed between the electrodes. Such devices are described in, for example, GB 1576474 and PCT/GB92/01313. In the latter of these an ionising ultra-violet light is passed through a gas-carrying airstream which then passes between two co-axial potentially biased annular electrodes, ionisation being substantially completed before the airflow enters the gap between the electrodes. The device is calibrated so that the current between the electrodes provides a measure of the concentration of the test gas in the airstream.

In the device of PCT/GB92/01313 the airflow therethrough is driven by a fan. However, the device is intended to be used in the open air, where the airspeed may be affected by local wind effects. This can affect the results. It is therefore desirable that the airspeed through the device be known. Conventional airspeed measuring devices (i.e. pivot tubes, anemometers) tend to the disproportionately expensive or complicated, and also in some cases may disrupt the measurement process.

SUMMARY OF THE INVENTION

According to the present invention a gas detector includes structure defining a gas flow passage, means for passing an ultraviolet light beam across the passage, and first and second electrodes downstream of the ultra-violet light means, at least one of the first and second electrodes being in the form of a series of electrically separate segments extending in a downstream direction, the electrodes being connectable to potential applying means and to means whereby the current passing through each segment of a segmented electrode can be measured.

In use air containing a concentration of ionisable test gas is passed through the air passage and subjected to the beam of ultra-violet light which causes a degree of ionisation in the test gas. Potential is applied across the electrodes, which causes ions to be collected by the electrodes, the resultant currents being measured and the measurements passed to analysing means which compare the readings from consecutive segments to provide a measurement of the air speed through the passage and which also sum the segment readings to provide the concentration of the test gas. The measurement of air speed may be displayed, and will usually be used directly by the analysing means.

There may be only one segmented electrode, in which case the potential applied between the unsegmented electrode and the segments will be the same in each case, or both electrodes may be segmented, in which case different potentials can be applied between associated pairs of electrodes.

In one form of the invention the gas passage is rectangular and the segments are in the form of flat rectangular strips. In another form the gas passage is circular, the electrodes are in co-axial form as in PCT/GB92/01313, and the segments are in annular form, in the form of sections of a rod, or both.

The detector may be provided with means, such as a fan, for inducing airflow through the passage, or may rely on flow speed (for example wind speed, or air speed in a duct) to induce flow, in which case electrodes may be provided on each side of the ultra-violet light source to allow for flow in either direction through the passage.

It will be realised, of course, that measurement of velocity through the detector by analysing readings from consecutive segments of the electrodes will require prior calibration of the detector.

According to another aspect of the present invention a method of measuring the velocity of flow, of an airflow containing a test gas, through a detector of the type wherein the flow is passed through an Ultra Violet (UV) light beam and then between two potentially biassed electrodes, at least one of the electrodes being in the form of a series of electrically separate segments extending in a downstream direction, includes the steps of calibrating the detector, of passing the airflow through the UV light beam, and of comparing readings of currents caused by ions falling on consecutive segments.

Yet another aspect of the present invention might dispense with the need for calibration.

According to yet another aspect of the present invention a method of measuring the velocity of flow, of an airflow containing a test gas, through a detector of the type wherein the flow is passed through an Ultra Violet (UV) light beam and then between two potentially biassed electrodes, at least one of the electrodes being in the form of a series of electrically separate segments extending in a downstream direction, a subsequent current across the electrodes being measured, includes the step of pulsing the UV light beam and noting a time interval between a pulse and response to the pulse as indicated by a sudden change in the current measurement caused by ions being collected by at least one of the segments.

In a conventional gas detector operating on the photo-ionisation principle, and ultra-violet radiation source is continuously maintained so as to produce a constant intensity and uninterrupted source of ultra-violet radiation to which the gas stream is exposed. The ultimate sensitivity of trace gas detection depends on the number of ions of the trace gas that can be created and collected by the combined system of ultra-violet radiation source and electrode collector means described above. At very low trace gas concentrations the ion current due to the ionised portion of the trace gas may become indistinguishable from the signal noise level in the system, and this determines the lower limit of detection of the device. Since only a small proportion of the available trace gas is in practice ionised, the number of ions produced can be increased in this operating range simply by increasing the power of the ultra-violet source so that a more intense flow of ultra violet radiation is produced, thereby producing more ions of the tracer gas, and thus increasing the lower limit of detection of the device. However, the simple expedient of increasing the power of the ultra-violet source whilst maintaining it in continuous emission has certain disadvantages such as:

i) the operating life of the ultra-violet source is likely to be significantly reduced by operating it continuously at higher power, and ii) for sources of the type in which ultra violet radiation passes via a transparent window into the gas stream, the problem of fouling of the window by products of the ionisation process is likely to be made worse, and iii) the power consumption of the device will be increased.

A feature of the pulsing process is that, as an addition to being used as a velocity measuring means, it can be used to provide enhanced lower limit sensitivity of trace gas detection, whilst overcoming to some extent the above problems.

In one such embodiment of the invention, an ultra-violet radiation source is provided by a gas discharge maintained in a cell by the passage of an electric current between electrodes embodied in the cell, or by the provision of a radio-frequency exciter circuit the inductive element of which surrounds the cell. Means are provided for turning the discharge on and off, or for causing the discharge to switch between two states of discharge distinguished by their differing power levels, at some specified frequency. During the high power segments of the discharge cycle, a high power pulse stream of ultra-violet radiation is produced, and this impinging on the trace gas in the airstream produces higher numbers of ions of the trace gas than at lower power levels.

The lower limit sensitivity of the device to the trace gas concentration is thus increased, approximately in proportion to the peak power level enhancement of the ultra violet radiation intensity over its equivalent continuous emission level.

The pulsating system also provides secondary advantages in that i) the overall power and duty cycle combination of the ultra-violet radiation source need not be significantly altered from its continuous mode characteristic, so that there need be no significant change in the useful lifetime of the ultra violet source, ii) the duty cycle of the ion production corresponds to a similar exposure of the source window to the products of ionisation as for the continuous mode of operation, so that fouling of the source window should not be worsened, and iii) the overall power requirements of the pulsed ultra-violet source need not be significantly greater than in its continuous-mode of operation.

In case of fluctuating concentrations the variation in concentration can of course be recovered from the output signal by the appropriate signal processing techniques.

The detector according to the present invention may be used, if desired, in conjunction with ultra-violet measuring means which measure the loss of ultra-violet from the beam crossing the gas flow passage. Such means are described in out co-pending Application PCT GB 93/02333 now assigned U.S. Ser. No. 08/436,273, filed on May 16, 1995, and now abandoned.

The electrodes may be positioned after a bend in the gas flow passage downstream of the ultra-violet light source as described in our co-pending Application GB 9226663.

BRIEF DESCRIPTION OF THE FIGURES

Some embodiments of the invention will now be described, by way of example only, with reference to the accompanying diagrammatic drawings, of which.

DETAILED DISCUSSION OF PREFERRED EMBODIMENTS

Figure 1:
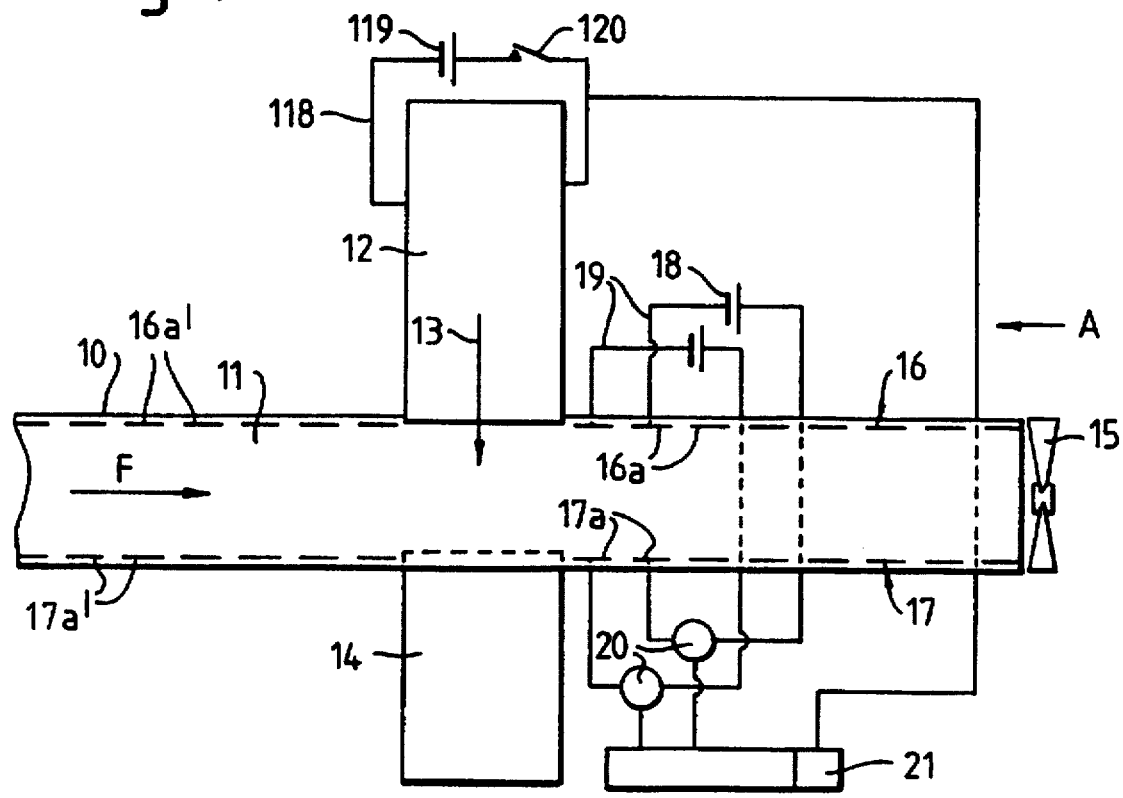
FIG. 1 is an elevation, in section along line I—I of FIG. 2, of a gas detector according to the invention.
Figure 2:
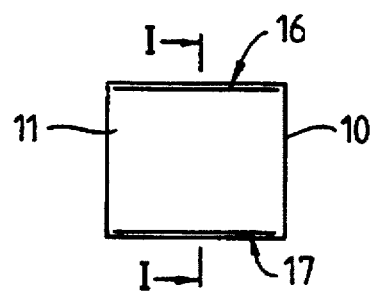
FIG. 2 is an end view, in the direction of arrow A in FIG. 1.
Figure 3:
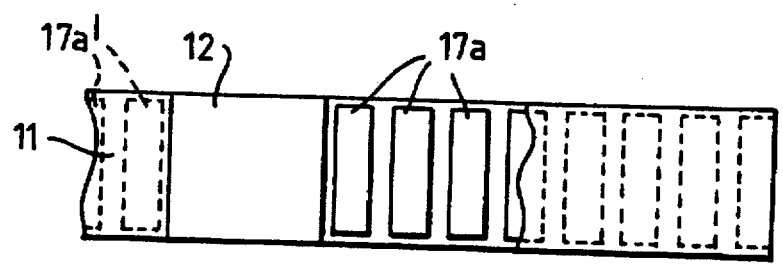
FIG. 3 is a plan view of part of the detector of FIG. 1.

A gas detector (FIGS. 1 to 3) has structure 10 defining a rectangular gas flow passage 11. An ultra-violet lamp 12 is positioned to send a beam 13 of ultra-violet light across the passage 11. An ultra-violet light loss measuring device 14, as described in PCT/GB 93/02333 may be positioned to collect light crossing the passage 11. A fan 15 is positioned at one end of the passage 11 to induce flow in the direction of arrow F through the passage 11, and downstream of the lamp 12 are two opposing electrodes 16, 17. The electrodes 16, 17 are divided into a plurality of paired segments 16a, 17a.

In use, each pair of electrodes is connected to a potential applying device (such as a battery) 18 in a circuit 19 which includes a current measuring device 20 whose readings are passed to a computer 21. The fan 15 is operated to induce flow of air through the passage 11 and the lamp 12 is operated to send a beam of light 13 across the flow. If the flow of air contains an ionisable test gas this is ionized by the beam 13 ad the resultant ions are collected by the electrodes 16, 17 causing readings to be taken by the current measuring devices 20. The readings of devices 20 from consecutive pairings of segments 16a, 17a, are compared by the computer 21 with calibrations to give the speed of flow through the passage 11 and the readings from all devices 20 are summed by the computer 21 and compared with calibrations (in which speed of flow will usually be a factor) to give the concentration of test gas in the flow.

Calibration is carried out by passing an airflow containing a test gas at various speeds through the flow passage 11, operating the UV lamp 18, applying a potential across the paired segments 16a, 17a of the electrodes 16, 17, and noting the current reading. The calibration can not conveniently be stored in the computer 21, For use in a pulsed mode the UV lamp can be powered by a supply 118 including power means 119 and a switch 120, the switch being operated by means controlled by the computer 21.

In a more complicated form of UV supply, an ultra-violet radiation source is provided by a gas discharge maintained in a cell by the passage of an electric current between electrodes embodied in the cell, or by the provision of a radio-frequency exciter circuit the inductive element of which surrounds the cell. The computer 21 controls means for turning the discharge on and off, or for causing the discharge to switch between two states of discharge distinguished by their differing power levels, at some specified frequency. During the high power segments of the discharge cycle, a high power pulse stream of ultra-violet radiation is produced, and this impinging on the trace gas in the airstream produces higher numbers of ions of the trace gas than at lower power levels.

For use with an airstream containing a single trace gas it will usually be unnecessary to calibrate the apparatus in the pulsed mode.

In use in the pulsed mode the time between a pulse and the change in reading due to ions being collected by a least one of the segments 16a, 17a is measured.

An alternative version of the device is adapted to cope with flow in either direction through the passage 11. The fan 15 is omitted, and electrodes 16', 17', which are mirror images of the electrodes 16, 17 are installed on the opposite side of the lamp 12 to the electrodes 16, 17.

One of the electrodes 16, 17 may be left unsegmented. In this case the potential between this electrode and each segment of the other electrode will be the same.

Figure 4:
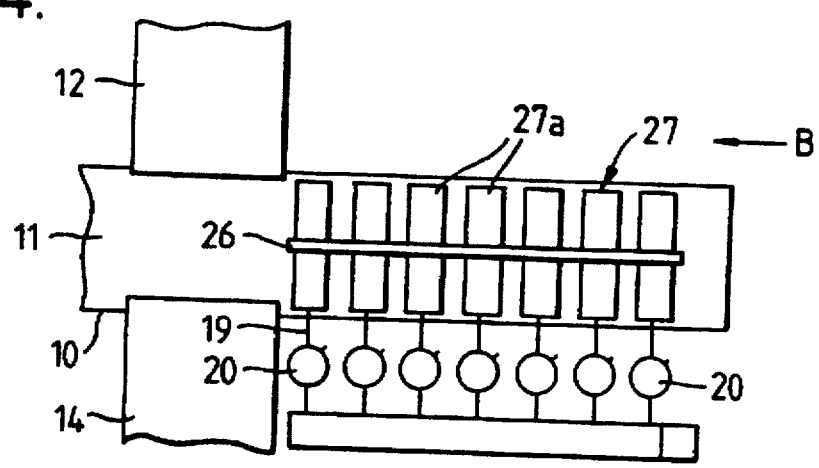
FIG. 4 is an elevation, in section along line IV—IV of FIG. 5, of another embodiment of the invention.
Figure 5:
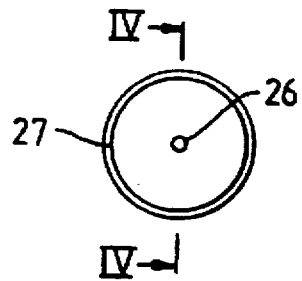
FIG. 5 is an end view in the direction of arrow B in FIG. 4.

In another embodiment of the invention (FIGS. 4 and 5) the configuration is the same other than that the gas flow passage 11 is of cylindrical section and the electrodes 26, 27 are co-axial, as in out co-pending PCT/GB92/01313. With this embodiment the central electrode, shown as 26, will usually be in the form of a rod and will usually be unsegmented. Constructional considerations are such that whilst an embodiment having a segmented central electrode is not impossible it is somewhat complicated. Segments 27a of the electrode 27 are of annular form.

Further embodiments within the scope of the invention will be apparent to those skilled in the art. For example unidirectional forms of the invention may have no fan therein, relying on flow speed such as wind speed or the speed of flow in a duct to induce flow therethrough.

Using the pulsed flow method it might be possible to calculate the concentrations of more than one test gas in an airstream by adjusting the rate of flow through the passage 13 such that ions of particular trace gases are collected substantially on different segments of the electrodes 16 17.

Further details of the operation of this type of gas detector are given in our various co-pending Applications mentioned above and will not be repeated here.

What is claimed is:

1. A method of measuring the velocity of flow, of an airflow containing a test gas, through a detector of the type wherein the flow is passed through an Ultra Violet (UV) light bean and then between two potentially biased electrodes, wherein at least one of the electrodes is in the form of a series of electrically separate segments extending in a downstream direction, said method including the steps of:

calibrating the detector passing the airflow through the UV light beam, comparing readings of currents caused by ions falling on consecutive segment to calibration currents and providing said flow velocity based upon said comparison.

2. A method as claimed in claim 1 further including the step of introducing airflow through a passage of the detector.

3. A method as claimed in claim 2 wherein said inducing step uses a fan.

4. A method as claimed in claim 3 wherein said inducing step includes using the fan to control the speed of flow through the passage.

5. A method as claimed in claim 1 further including the step of using air flow speed to induce flow through a passage of the detector.

6. A method as claimed in claim 5 are used on each side of an ultra-violet light source for permitting flow in either direction through the passage.

7. A method as claimed in claim 1 wherein the detector is used in conjunction with ultra-violet measuring means which measure the loss of ultra-violet from the beam crossing the gas flow passage.

8. A method as claimed in claim 1 and further including the steps of:

summing the readings of currents caused by ions falling on all segments; and comparing said sum of the readings with calibration data to provide a measure of concentration of test gas in the airflow.

* * * * *